United States Patent [19]

Enami et al.

[11] Patent Number: 5,239,085
[45] Date of Patent: Aug. 24, 1993

[54] ORGANOCYCLOSILOXANE AND METHOD FOR ITS PREPARATION

[75] Inventors: Hiroji Enami; Shoji Akamatsu, both of Chiba, Japan

[73] Assignee: Dow Corning Toray Silicone Co., Ltd., Tokyo, Japan

[21] Appl. No.: 842,292

[22] Filed: Feb. 26, 1992

[30] Foreign Application Priority Data

Mar. 6, 1991 [JP] Japan .................................. 3-065477

[51] Int. Cl.$^5$ ........................... C07F 7/08; C07F 7/10; C07F 7/18
[52] U.S. Cl. ................... 549/215; 556/410; 556/434; 556/439; 556/449; 556/460; 556/461
[58] Field of Search ............... 549/215; 556/439, 410, 556/449, 460, 461, 434

[56] References Cited

U.S. PATENT DOCUMENTS

| | | | |
|---|---|---|---|
| 4,208,503 | 6/1980 | Martin | 549/215 X |
| 4,587,354 | 5/1986 | Takago | 556/417 |
| 4,689,085 | 8/1987 | Plueddemann | 106/287.14 |
| 4,804,768 | 2/1989 | Quirk et al. | 549/215 |
| 5,037,861 | 8/1991 | Crivello et al. | 549/215 X |
| 5,115,069 | 5/1992 | Motegi et al. | 549/215 X |

FOREIGN PATENT DOCUMENTS 30300 5/1986 Japan .
163887 2/1992 Japan .

Primary Examiner—Paul F. Shaver
Attorney, Agent, or Firm—Alex Weitz

[57] ABSTRACT

An organocyclosiloxane having utility as a coupling agent is disclosed said organocyclosiloxane having the general formula

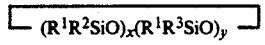

$$(R^1R^2SiO)_x(R^1R^3SiO)_y$$

wherein $R^1$ is independently selected from monovalent hydrocarbon groups having 1 to 8 carbons, $R^2$ is selected from the group consisting of an alkoxy group and an alkoxysilylalkyl group, $R^3$ is an organofunctional group selected from the group consisting of glycidoxyalkyl, methacryloxyalkyl, N-(trialkylsilyl)aminoalkyl (hydroxyphenyl)alkyl and haloalkyl x is 1 to 6 and y is 1 to 6, with the proviso that $x+y$ is an integer having a value of 3 to 8.

11 Claims, No Drawings

ORGANOCYCLOSILOXANE AND METHOD FOR ITS PREPARATION

FIELD OF THE INVENTION

The present invention relates to a novel organocyclosiloxane, and, more particularly, relates to an organocyclosiloxane which contains both silicon-bonded alkoxy and organofunctional groups in each molecule.

BACKGROUND OF THE INVENTION

Various types of organofunctional group-containing organocyclosiloxanes are already known. For example reference is made to the azide-containing cyclic polyorganosiloxane disclosed in Japanese Patent Application Laid Open (Kokai or Unexamined) Number 54-30300, the cyclosiloxane derivative disclosed in Japanese Patent Application Laid Open Number 60-163887 and the difunctional organocyclosiloxane disclosed in Japanese Patent Publication Number 63-18977. With regard to organocyclosiloxane which contains silicon-bonded alkoxy, reference is made to the disilyl crosslinking compound disclosed in Japanese Patent Application Laid Open Number 64-6036. However organocyclosiloxane which contains both silicon-bonded alkoxy and organofunctional groups within each molecule has remained unknown.

SUMMARY OF THE INVENTION

The present inventors carried out extensive investigations with regard to organocyclosiloxane which contain both silicon-bonded alkoxy and organofunctional groups within each molecule, and the present invention was developed as a result.

Thus, the present invention takes as its object the introduction of organocyclosiloxane which contains both silicon-bonded alkoxy and organofunctional groups within each molecule which is a novel compound, as well as the introduction of a method for the preparation of same.

The object of the present invention is achieved by means of an organocyclosiloxane having the following general formula

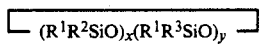  (I)

wherein $R^1$ is a monovalent hydrocarbon group having 1 to 8 carbons, $R^2$ is an alkoxy or alkoxysilylalkyl group, $R^3$ is an organofunctional group selected from the group consisting of glycidoxyalkyl methacryloxyalkyl, N-(trialkylsilyl)aminoalkyl, (hydroxyphenyl)alkyl and haloalkyl, x is 1 to 6, y is 1 to 6 and x+y is an integer with a value of 3 to 8.

DETAILED DESCRIPTION OF THE INVENTION

The group $R^1$ in formula (I) is an independently selected monovalent hydrocarbon group having 1 to 8 carbon atoms. This group is concretely exemplified by alkyl groups such as methyl, ethyl, propyl, and butyl; aryl groups such as phenyl and tolyl and substituted alkyl groups such as chloromethyl and 3,3,3-trifluoropropyl, A range of 1 to 8 is specified for the number of carbons in $R^1$ because the industrial production of the organocyclosiloxane becomes highly problematic when $R^1$ contains more than 8 carbons. $R^1$ is preferably methyl in the organocyclosiloxane of the present invention.

The group $R^2$ in the preceding formula comprises an alkoxy group, as exemplified by methoxy and ethoxy or an (alkoxysilyl)alkyl group, as exemplified by (trimethoxysilyl)ethyl, (trimethoxysilyl)propyl, (methyldimethoxysilyl)ethyl (triethoxysilyl)ethyl (triethoxysilyl)propyl, and (diethoxymethylsilyl)ethyl. $R^2$ is an essential organic group for the organocyclosiloxane according to the present invention, and it is this group which gives the organocyclosiloxane according to the present invention a characteristic and excellent reactivity for inorganics when this organocyclosiloxane is used as a silane coupling agent.

The group $R^3$ in the preceding formula comprises an organofunctional group selected from glycidoxyalkyl groups, methacryloxyalkyl groups, N-(trialkylsilyl)aminoalkyl groups, (hydroxyphenyl)alkyl groups, and haloalkyl groups. Concrete examples in this regard are glycidoxyethyl and glycidoxypropyl for the glycidoxyalkyl groups: methacryloxyethyl and methacryloxypropyl for the methacryloxyalkyl groups; N-(trimethylsilyl)aminopropyl and N-(triethylsilyl)aminopropyl for the N-(trialkylsilyl)aminoalkyl groups: o-(hydroxyphenyl)propyl, m-(hydroxyphenyl)propyl, and p-(hydroxyphenyl)propyl for the (hydroxyphenyl)alkyl groups: and chloropropyl and chlorobutyl for the haloalkyl groups. The organocyclosiloxane according to the present invention may contain more than one type of the aforementioned organofunctional groups. Like $R^2$, the group $R^3$ is an essential organic group for the organocyclosiloxane according to the present invention, and it is this group which provides the organocyclosiloxane according to the present invention with a characteristic and excellent reactivity with and affinity for organic resin when the organocyclosiloxane according to the present invention is added to organic resin.

The subscripts x and y in formula (I) represent, respectively, the number of $R^2$-containing siloxane units and the number of $R^3$-containing siloxane units within the single molecule of the organocyclosiloxane according to the present invention. The x and y are each integers with values in the range of 1 to 6, and the sum of x plus y must be an integer with a value in the range of 3 to 8. The organocyclosiloxane does not exist for a sum of x+y of less than 3, while post-production purification of the organocyclosiloxane becomes problematic when the sum of x+y exceeds 8.

The following compounds are provided as examples of organocyclosiloxane according to the present invention.

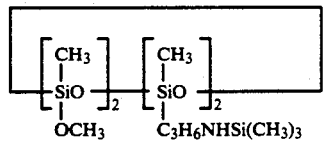

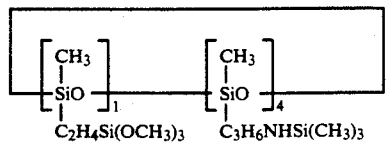

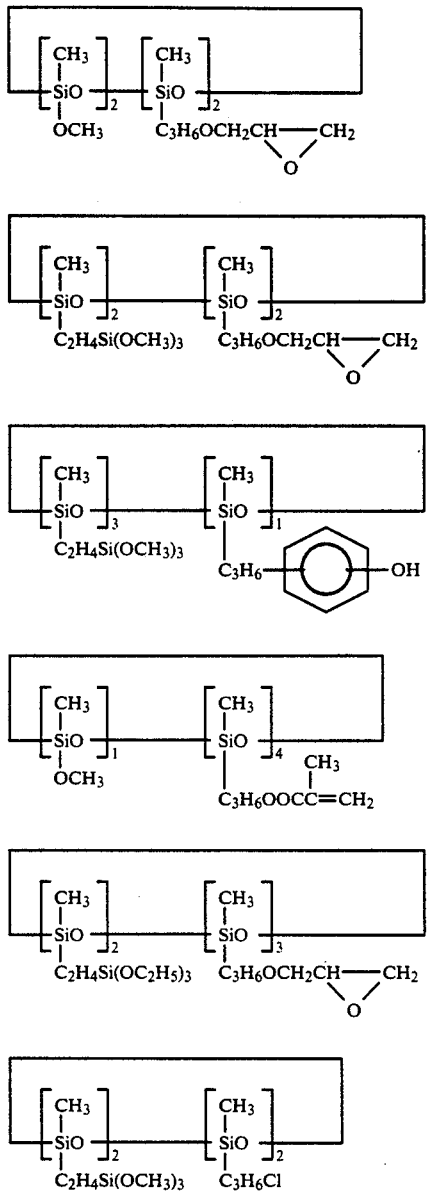

The organocyclosiloxane according to the present invention can be prepared by the reaction of
(A) an organohydrogencyclosiloxane with the following general formula $$(R^1HSiO)_z \qquad (II)$$

wherein $R^1$ is a monovalent hydrocarbon group having 1 to 8 carbon atoms and z is an integer with a value of 3 to 8, (B) an organic compound selected from the group consisting of glycidoxyalkenes methacryloxyalkenes, N-(trialkylsilyl)aminoalkenes, (hydroxyphenyl)alkenes, and haloalkenes, wherein at least 1 mole of component (B) is added per 1 mole component (A), and (C) an alcohol or alkoxysilyl-containing unsaturated hydrocarbon wherein at least 1 mole of component (C) is added per 1 mole component (A) in the presence of (D) a hydrosilylation-reaction catalyst.

The organohydrogencyclosiloxane comprising component (A) is the principal starting material for the organocyclosiloxane according to the present invention and the former is expressed by the general formula (II). In formula (II), z corresponds to the number of organohydrogensiloxane units in the organohydrogencyclosiloxane and it should be an integer with a value in the range of 3 to 8. This range is specified for the value of z because the organohydrogencyclosiloxane cannot exist when z is less than 3. On the other hand, when z exceeds 8, industrial synthesis of the organohydrogencyclosiloxane becomes problematic and purification of the organocyclosiloxane is impaired. The organohydrogencyclosiloxane comprising component (A) is concretely exemplified by 1,3,5,7-tetramethylcyclotetrasiloxane and 1,3,5 7,9-pentamethylcyclopentasiloxane.

Component (B) is an organic compound which is selected from glycidoxyalkenes, methacryloxyalkenes, N-(trialkylsilyl)aminoalkenes, (hydroxyphenyl)alkenes or haloalkenes. Concrete examples of this component are as follows, glycidoxyvinyl and glycidoxyallyl for the glycidoxyalkenes methacryloxyvinyl and methacryloxyallyl for the methacryloxyalkenes N-(trimethylsilyl)aminoallyl and N-(triethylsilyl)aminoallyl for the N-(trialkylsilyl)aminoalkenes; o-(hydroxyphenyl)allyl and p-(hydroxyphenyl)allyl for the (hydroxyphenyl)alkenes; and 3-chloroallyl for the haloalkenes. The organocyclosiloxane according to the present invention is produced by the reaction of the silicon-bonded hydrogen atoms in component (A) with this organic compound comprising component (B) as well as with component (C) (alcohol or alkoxysilyl-containing unsaturated hydrocarbon) in the presence of component (D). At least 1 mole component (B) should be added in the preparative method according to the present invention per 1 mole component (A). The yield of organocyclosiloxane according to the present invention is substantially reduced when less than 1 mole component (B) is used per mole component (A).

Component (C) comprises alcohols and alkoxysilyl-containing unsaturated hydrocarbons, and this component is concretely exemplified by methanol and ethanol for the alcohols and by vinyltrimethoxysilane, allyltrimethoxysilane, methylvinyldimethoxysilane vinyltriethoxysilane, and allyltriethoxysilane for the alkoxysilyl-containing unsaturated hydrocarbons. The organocyclosiloxane according to the present invention is synthesized by the reaction of the silicon-bonded hydrogen atoms in component (A) with the alcohol or alkoxysilyl-containing unsaturated hydrocarbon comprising component (C) as well as with component (B) in the presence of component (D). At least 1 mole component (C) should be added in the preparative method according to the present invention per 1 mole component (A). The yield of organocyclosiloxane according to the present invention is substantially reduced when less than 1 mole component (C) is added per mole component (A).

The hydrosilylation-reaction catalyst comprising component (D) functions as a catalyst which accelerates the reaction of the silicon-bonded hydrogen atoms on component (A) with components (B) and (C). While component (D) may take the form of any hydrosilylation-reaction catalyst in general use, platinum-type catalysts are particularly preferred. Said platinum-type catalysts are exemplified by platinum black platinum on-carbon, chloroplatinic acid, alcohol solutions of chloroplatinic acid, chloroplatinic acid/olefin complexes, and chloroplatinic acid/vinylsiloxane complexes. Component (D) should be added in the invention's preparative method in a generally employed catalytic quantity. When component (D) takes the form of a platinum-type catalyst, it is preferably used within the range of 10 to 1,000 ppm as platinum metal atoms referred to the total weight of components (A) plus (B) plus (C).

The reaction temperature is not specifically restricted for the preparative method according to the present invention, but temperatures in the range of 40° to 150° C. are generally preferred. When the reaction temperature falls below 40° C, the yield of organocyclosiloxane according to the present invention is reduced. This is a consequence of a selective reaction of component (B) with component (A), which occurs because the component (A)+component (B) reaction rate is faster than the component (A)+component (C) reaction rate at such temperatures. Secondary reactions tend to occur when the reaction temperature exceeds about 150° C., and this also reduces the yield of the organocyclosiloxane according to the present invention.

The use of solvent is optional in the preparative method according to the present invention. No particular restriction is placed on organic solvents which may be employed by the present invention, but nonpolar organic solvents such as toluene and xylene are preferred.

The molecular structure of the organocyclosiloxane according to the present invention can be determined by various analytical methods. Thus for example the functional groups in the organocyclosiloxane according to the present invention can be determined by nuclear magnetic resonance spectral analysis, infrared absorption spectral analysis, or ultraviolet absorption spectral analysis.

Because each molecule contains Si-bonded alkoxy and organofunctional groups, the organocyclosiloxane according to the present invention is an effective silane coupling agent. The corresponding surface properties, mechanical properties, and electrical properties are improved through its application to the surface of glass fiber or inorganics or through its addition to various types of plastics.

EXAMPLES

The present invention will be explained in greater detail through the following illustrative examples.

EXAMPLE 1

Two hundred and forty grams of 1,3,5,7-tetramethylcyclotetrasiloxane (approximately 1 mole) and 0.01 g of chloroplatinic acid were introduced with mixing into a stirrer-equipped one liter roundbottom flask. This was followed by heating to 50° C. A liquid mixture of 239 g of allyl glycidyl ether (approximately 2 moles) and 310 g of vinyltrimethoxysilane (approximately 2 moles) was added dropwise from an addition funnel over 4 hours. The temperature of the reaction solution during this interval was 50° to 80° C. The reaction solution was then heated to 80° to 100° C. and stirred for an additional one hour. The reaction solution was then brought to 20 mmHg/80° C. and stripped for 1 hour in order to remove unreacted starting material. Stripping afforded 710 g of a product in the form of a light yellow, transparent liquid.

This product was submitted to infrared absorption spectroscopic analysis and nuclear magnetic resonance spectroscopic analysis, and the results confirmed the product to be an organocyclosiloxane with the following average formula:

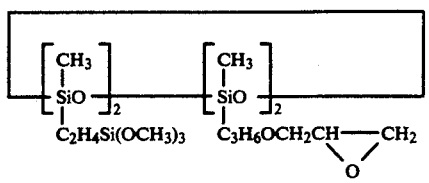

EXAMPLE 2

Two hundred and forty grams of 1,3,5,7-tetramethylcyclotetrasiloxane (approximately 1 mole) and 0.01 g of chloroplatinic acid were introduced with mixing into a stirrer-equipped 1 L roundbottom flask. This was followed by heating to 50° C. A liquid mixture of 279 g of 2-allylphenol (approximately 2 moles) and 310 g of vinyltrimethoxysilane (approximately 2 moles) was added dropwise from an addition funnel over 4 hours. The temperature of the reaction solution during this interval was 50° to 80° C. The reaction solution was then heated to 80° to 100° C. and stirred for an additional 1 hour. The reaction solution was then brought to 5 mmHg/110° C. and stripped for 1 hour in order to remove unreacted starting material. Stripping afforded 740 g of a product in the form of a light yellow, transparent liquid.

This product was submitted to infrared absorption spectroscopic analysis and nuclear magnetic resonance spectroscopic analysis, and the results confirmed the product to be an organocyclosiloxane with the following average formula:

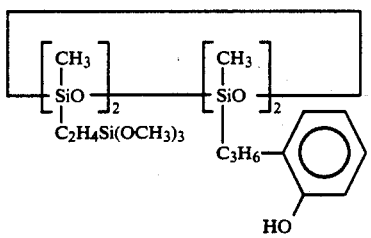

EXAMPLE 3

Two hundred and forty grams of 1,3,5,7-tetramethylcyclotetrasiloxane (approximately 1 mole) and 0.091 g of chloroplatinic acid were introduced with mixing into a stirrer-equipped 1 L roundbottom flask. This was followed by heating to 50° C. There was added dropwise from an additional funnel over 4 hours 342 grams of allyl glycidyl ether (approximately 3 moles). The temperature of the reaction solution during this interval was 50° to 80° C. The reaction mixture was then heated to 80° to 100° C. and stirred for an additional 1 hour.

Three hundred and fifty grams of methanol and 3.5 g of sodium bicarbonate were introduced into a stirrer-equipped 1 L roundbottom flask. The preceding reaction mixture was then dripped into this from an addition funnel over a 6 hour period while heating under reflux. The evolution of hydrogen due to the dehydrogenation reaction was observed. After the completion of addition, heating under reflux was continued for 3 hours at which point hydrogen evolution had ceased. The reaction solution was then brought to 20 mmHg/110° C. and stripped for 1 hour in order to remove unreacted starting material Stripping was followed by pressure filtration to yield 560 g of a light yellow, transparent liquid product.

The obtained product was submitted to infrared absorption spectroscopic analysis and nuclear magnetic resonance spectroscopic analysis, and the results confirmed the product to be an organocyclosiloxane with the following average formula:

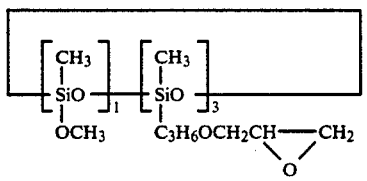

EXAMPLE 4

Two hundred and forty grams of 1,3,5,7-tetramethylcyclotetrasiloxane (approximately 1 mole) and 0.01 g of chloroplatinic acid were introduced with mixing into a stirrer-equipped 1 L roundbottom flask. This was followed by heating to 50° C. A liquid mixture of 126 g of allyl methacrylate (approximately 1 mole) and 465 g of vinyltrimethoxysilane (approximately 3 moles) was added dropwise from an addition funnel over 4 hours. The temperature of the reaction solution during this interval was 50° to 60° C. The reaction solution was then heated to 50° to 60° C. and stirred for an additional 1 hour. The reaction solution was then brought to 2 mmHg/60° C. and stripped for 1 hour in order to remove unreacted starting material Stripping afforded 745 g of a product in the form of a light yellow, transparent liquid.

The obtained product was submitted to infrared absorption spectroscopic analysis and nuclear magnetic resonance spectroscopic analysis, and the results confirmed the product to be an organocyclosiloxane with the following average formula:

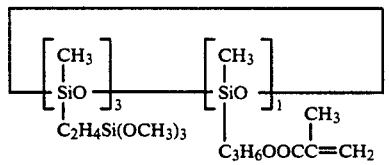

That which is claimed is:

1. An organocyclosiloxane having the following general formula

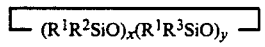

wherein $R^1$ is independently selected from monovalent hydrocarbon groups having 1 to 8 carbons $R^2$ is selected from the group consisting of an alkoxy group and an alkoxysilylalkyl group, $R^3$ is an organofunctional group selected from the group consisting of glycidoxyalkyl, methacryloxyalkyl N-(trialkylsilyl)aminoalkyl (hydroxyphenyl)alkyl and haloalkyl x is 1 to 6 and y is 1 to 6, with the proviso that $x+y$ is an integer having a value of 3 to 8.

2. The organocyclosiloxane according to claim 1, wherein $R^1$ is selected from the group consisting of methyl, ethyl, propyl, butyl, phenyl, chloromethyl and 3,3,3-trifluoropropyl.

3. The organocyclosiloxane according to claim 2, wherein $R^2$ is selected from the group consisting of methoxy, ethoxy, (trimethoxysilyl)ethyl, (trimethoxysilyl)propyl, (methyldimethoxysilyl)ethyl, (triethoxysilyl)ethyl, (triethoxysilyl)propyl and (diethoxymethylsilyl)ethyl.

4. The organocyclosiloxane according to claim 3, wherein $R^3$ is selected from the group consisting of glycidoxyethyl, glycidoxypropyl, methacryloxyethyl, methacryloxypropyl, N-(trimethylsilyl)aminopropyl, N-(triethylsilyl)aminopropyl, o-(hydroxyphenyl)propyl, m-(hydroxyphenyl)propyl, p-(hydroxyphenyl)propyl, chloropropyl and chlorobutyl.

5. The organocyclosiloxane according to claim 1, wherein $R^1$ is a methyl radical.

6. The organocyclosiloxane according to claim 3, wherein $R^1$ is a methyl radical.

7. The organocyclosiloxane according to claim 4, wherein $R^1$ is a methyl radical.

8. A method for the preparation of an organocyclosiloxane having the following general formula

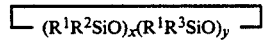

wherein $R^1$ is independently selected from monovalent hydrocarbon groups having 1 to 8 carbons, $R^2$ is selected from the group consisting of an alkoxy group and an alkoxysilylalkyl group, $R^3$ is an organofunctional group selected from the group consisting of glycidoxyalkyl, methacryloxyalkyl, N-(trialkylsilyl)aminoalkyl, (hydroxyphenyl)alkyl and haloalkyl, x is 1 to 6 and y is 1 to 6, with the proviso that $x+y$ is an integer having a value of 3 to 8 by reacting, (A) an organohydrogencyclosiloxane with the following general formula

wherein $R^1$ is a monovalent hydrocarbon group having 1 to 8 carbon atoms and z is an integer with a value of 3 to 8;

(B) an organic compound selected from the group consisting of glycidoxyalkenes, methacryloxyalkenes, N-(trialkylsilyl)aminoalkenes, (hydroxyphenyl)alkenes, and haloalkenes, wherein at least 1 mole of component (B) is added per 1 mole of component (A); and (C) an alcohol or alkoxysilyl-containing unsaturated hydrocarbon wherein at least 1 mole of component (C) is added per 1 mole component of (A) in the presence of (D) a hydrosilylation-reaction catalyst.

9. The method according to claim 8 wherein $R^1$ is selected from the group consisting of methyl, ethyl, propyl, butyl, phenyl, chloromethyl and 3,3,3-trifluoropropyl.

10. The method according to claim 9, wherein $R^2$ is selected from the group consisting of methoxy, ethoxy, (trimethoxysilyl)ethyl, (trimethoxysilyl)propyl, (methyldimethoxysilyl)ethyl, (triethoxysilyl)ethyl, (triethoxysilyl)propyl and (diethoxymethylsilyl)ethyl.

11. The method according to claim 10, wherein $R^3$ is selected from the group consisting of glycidoxyethyl, glycidoxypropyl, methacryloxyethyl, methacryloxypropyl, N-(trimethylsilyl)aminopropyl, N-(triethylsilyl)aminopropyl, o-(hydroxyphenyl)propyl, m-(hydroxyphenyl)propyl, p-(hydroxyphenyl)propyl, chloropropyl and chlorobutyl.

* * * * *